United States Patent
Redol

(10) Patent No.: US 10,226,609 B2
(45) Date of Patent: Mar. 12, 2019

(54) DISPENSING MECHANISM FOR DELIVERY OF PHARMACEUTICAL FORMS INTO BODY HOLES AND APPLICATOR COMPRISING THE SAME

(71) Applicant: BEYONDEVICES LDA, Sobral Monte Agraco (PT)

(72) Inventor: Rui Carlos Ribeiro Redol, Sintra (PT)

(73) Assignee: BEYONDDEVICES LDA, Sobral Monte Agraco (PT)

( * ) Notice: Subject to any disclaimer, the term of this patent is extended or adjusted under 35 U.S.C. 154(b) by 210 days.

(21) Appl. No.: 14/438,728

(22) PCT Filed: Oct. 23, 2013

(86) PCT No.: PCT/PT2013/000061
§ 371 (c)(1),
(2) Date: Apr. 27, 2015

(87) PCT Pub. No.: WO2014/065685
PCT Pub. Date: May 1, 2014

(65) Prior Publication Data
US 2015/0290440 A1    Oct. 15, 2015

(30) Foreign Application Priority Data
Oct. 26, 2012    (PT) .......................................... 106603

(51) Int. Cl.
*A61M 31/00*    (2006.01)
*A61F 6/18*    (2006.01)
(Continued)

(52) U.S. Cl.
CPC ........... *A61M 31/007* (2013.01); *A61B 50/30* (2016.02); *A61D 7/00* (2013.01); *A61F 6/06* (2013.01); *A61F 6/18* (2013.01); *A61M 31/00* (2013.01)

(58) Field of Classification Search
CPC ................ A61M 31/007; A61M 31/00; A61M 37/0069; A61F 6/06; A61F 6/12; A61F 6/18; A61D 7/00; A61B 50/30
See application file for complete search history.

(56) References Cited

U.S. PATENT DOCUMENTS 3,394,699 A * 7/1968 Koett ..................... A61B 10/04
                                                        600/572
3,934,584 A * 1/1976 Corio ....................... A61D 7/00
                                                        604/59
(Continued)

FOREIGN PATENT DOCUMENTS

DE        1803146         5/1970
DE        1803146 A1 *    5/1970 .......... A61M 31/007
(Continued)

*Primary Examiner* — Bhisma Mehta
*Assistant Examiner* — Jenna Zhang
(74) *Attorney, Agent, or Firm* — Porzio Bromberg & Newman P.C.

(57) ABSTRACT

The present invention relates to a dispensing mechanism (2) for delivery of pharmaceutical forms (4) into body holes and an applicator (I) comprising the novel dispensing mechanism (2). The pharmaceutical form dispensing mechanism (2) Comprises a rod (2A) connected to a flexible member (2B). One end of the rod is free from constraints in order to allow its axial movement. The other end of the rod is cooperatively connected to said flexible member (2B). The flexible member has a rounded or angular shape, being able to be deformed and being provided with shape memory. The flexible member (2B) extends in a direction perpendicular to the direction of a compression force applied to it and recovers its original shape when said compression force is withdrawn, thereby imparting, respectively, a forward or rearward movement to the rod (2A), namely when a part (2C) thereof is immobilized in the body (3) of the applicator.

12 Claims, 4 Drawing Sheets

(51) Int. Cl.
*A61D 7/00* (2006.01)
*A61F 6/06* (2006.01)
*A61B 50/30* (2016.01)

(56) References Cited

U.S. PATENT DOCUMENTS

| | | | | |
|---|---|---|---|---|
| 4,043,338 A | * | 8/1977 | Homm | A61M 25/04 |
| | | | | 604/105 |
| 4,904,244 A | * | 2/1990 | Harsh | A61M 5/3205 |
| | | | | 604/110 |
| 5,295,972 A | * | 3/1994 | Mischenko | A61M 5/3275 |
| | | | | 604/192 |
| 5,571,071 A | * | 11/1996 | Shapiro | A61B 1/267 |
| | | | | 600/185 |
| 5,681,279 A | * | 10/1997 | Roper | A61D 7/00 |
| | | | | 604/57 |
| 5,707,362 A | * | 1/1998 | Yoon | A61B 17/3417 |
| | | | | 604/164.03 |
| 5,749,886 A | * | 5/1998 | Abidin | A61B 17/3211 |
| | | | | 30/162 |
| 5,861,024 A | * | 1/1999 | Rashidi | A61B 18/1492 |
| | | | | 600/374 |
| 8,583,260 B2 | * | 11/2013 | Knudson | A61M 25/0136 |
| | | | | 600/374 |
| 2003/0158511 A1 | * | 8/2003 | Shue | A61F 13/26 |
| | | | | 604/17 |
| 2003/0233077 A1 | | 12/2003 | Swick | |
| 2004/0249352 A1 | * | 12/2004 | Swick | A61F 13/26 |
| | | | | 604/279 |
| 2006/0084964 A1 | * | 4/2006 | Knudson | A61M 25/0122 |
| | | | | 606/41 |

FOREIGN PATENT DOCUMENTS

| | | | | |
|---|---|---|---|---|
| DE | | 1803146 A1 * | 5/1970 | A61M 31/007 |
| WO | | WO 03101525 A1 * | 12/2003 | A61M 31/007 |
| WO | | WO-03101525 A1 * | 12/2003 | A61M 31/007 |

* cited by examiner

DISPENSING MECHANISM FOR DELIVERY OF PHARMACEUTICAL FORMS INTO BODY HOLES AND APPLICATOR COMPRISING THE SAME

FIELD OF THE INVENTION

The present invention relates to a dispensing mechanism for a delivery applicator of pharmaceutical forms into body holes, namely via vaginal, anal and nasal routes, and particularly for intravaginal delivery. The invention further relates to an applicator comprising the novel pharmaceutical form dispensing mechanism.

BACKGROUND OF THE INVENTION

Dispensing drugs through body holes, namely vaginal, anal and nasal delivery, is a widespread and common practice in the art.

Regarding to delivery by anal or vaginal route, this implies operational procedures which impart an overall feeling of discomfort to its users, whereby it represents opportunities for improvement that provide a positive impact among its potential users.

In particular, women represent more than half of world's population and they may suffer from diseases specific to their gender that despite not normally being life-threatening can result in a sharp decrease in quality of life. Several companies are developing new therapies in order to solve these problems and improve the quality of life of women.

The vaginal route has been traditionally used for local delivery of drugs, but is now much more relevant as a plausible route for systemic delivery. The delivery of drugs by vaginal route is usually useful for the prevention and treatment of sexually transmitted diseases and for contraceptives, but new developments in the field of bio-adhesives and liposomes indicate that this might be a useful route to other therapies.

The advantages of delivering drugs through vaginal route are the ease of delivery, the possibility of self-delivery, low systemic exposure to the drug and good permeability to some drugs when compared with other routes of delivery. The low enzyme activity and the possibility for absorbed drug being transferred into the uterus may also benefit the delivery of the drug.

For intra-vaginal delivery of drugs is necessary to use suitable devices. The design of devices for vaginal route delivery should take into account the anatomical and physiological aspects of the vagina. Traditionally, pharmaceutical forms comprise liquids (solutions, emulsions or suspensions), vaginal suppositories or ovula, as well as tablets, capsules or even creams and gels.

Such devices for vaginal route delivery, also commonly named applicators, should allow the correct and properly located application of the drug to be used in the vagina. Delivery through vaginal route requires that applicators are inserted into the vagina, adequately deposit the drug, and then being removed. Since they can produce changes in the mucosa, it is essential that devices assure a level of security that should be evaluated as integral part of vaginal products.

Applicators can be divided into two major groups: disposable (single use) and reusable ones. Generally, single-use applicators are already filled with the drug and properly packaged into blisters while the reusable ones are filled with drug by the user prior to use.

Various designs of such devices are already known in the art, particularly plunger devices or toothpaste shaped tubes, wherein not all of which allow for easy and comfortable insertion, due to the presence of sharp edges.

The design of such applicators should have as main assumptions:

safety, for example in relation to chemical and physical stability of the drug, or seeking prevention of localized trauma associated with its use, and in particular to its insertion;

efficiency, evaluated, e.g., by adequate and consistent localized delivery of the required drug dosage;

acceptance, taking into account the comfort, ease of use and aesthetic aspects.

Prior art applicators are very rigid and their insertion end may damage the vaginal mucosa. Also, the uneven end of usual applicators collides painfully with vaginal walls while pushing them away against the intra-abdominal forces.

Usual applicators have no insertion depth control, being easily inserted excessively, causing pain and potentially damaging the ostium, which will become especially dangerous during pregnancy.

Finally, in applicators of the prior art, the plunger of the applicator, when the latter is filled and ready for insertion, is located away from the anatomical extent of the user's hand. This cause the user to adopt anatomically incorrect body positions in order to operate the device, as well as requiring the use of both hands. Moreover, the use of applicators of the prior art requires that the patient must rest in a lying position with legs bent, not allowing, for example, its use in the sitting position.

The following is a brief description of devices for delivery of drugs through vaginal route disclosed in prior art documents closer to the present invention.

Patent Application U.S. 2003233077 A1 entitled "Applicator Device for Suppositories and the Like" discloses an applicator for dispensing pharmaceutical products, having a fusiform shape and comprising a body and a plunger for release of ovula.

European Patent EP 1518574 B1, entitled "Cannula for Dispensing Fluid Products for Vaginal and Anal Applications" discloses a cannula for dispensing fluids, for vaginal application, comprising a tubular body and a plunger allowing a controlled release of the drug.

Patent Application U.S. 2003158511 A1 entitled "Vaginal Suppository Delivery Device" discloses a device for dispensing suppositories through vaginal route including a forceps shaped body having upper and lower attachment members cooperating together to confine a passage, a sleeve member and a plunger.

Patent Application U.S. Pat. No. 4,312,347 A, entitled "Positive Pressure Drug Releasing Device" discloses a device for extended delivery of drug for intra-vaginal or intra-uterine drug release. The device has a body including a plunger driven by a compression spring which generates a pressure for expelling the drug in liquid form out of the body defining chamber. At one end of the body there is a membrane restricting the drug delivery flow rate, to provide the patient with the prescribed dosage.

There are further patent documents on the same technical field, such as for example, EP 0910427 B1, EP 1319420 A1, although they do not disclose the technical features of the present invention. Further, they are not as useful as the present solution and they do not provide similar easiness of use as the solution disclosed herein.

In view of the above, there is a need for a delivery device (or applicator) and pharmaceutical forms dispensing mechanism thereof providing for:

manufacture simplicity, for example, due to a dispensing mechanism made of a single part;

simplicity of operation and ergonomics for easy handling and use with only one hand, while providing a comfortable operation;

safety, ensuring the body integrity, namely the vaginal mucosa, and an adequate depth of insertion;

efficiency, ensuring an accurate delivery at the desired location, and versatility, allowing for a broad use of different pharmaceutical forms to be dispensed, such as, for example, tablets, ovula, capsules, pills, gels, suspensions, and suppositories.

SUMMARY OF THE INVENTION

The present invention relates to a pharmaceutical form dispensing mechanism (2) comprising a rod (2A) having a first end and a second end, characterized in that it further comprises:

a flexible member (2B), connected to the first end of the rod (2A), which flexible member (2B) is able to be deformed and is provided with shape memory, and has a rounded or angular shape, and a flexible member part (2C) opposite to said first end of the rod (2A), which rod (2A) is connected to the flexible member (2B), wherein the flexible member (2B) extends in a direction perpendicular to the direction of a compression force applied to it for actuation, and recovers its original shape when said compression force is withdrawn, thereby imparting a displacement to the rod (2A) to which it is connected, and providing, respectively, a forward or rearward axial movement to said rod (2A).

In one aspect of the invention, the flexible member (2B) has a shape selected from the group consisting in a ring, semi-circular, oval, semi-oval, spherical calotte and V shape.

In another aspect of the invention, the rod (2A) and the flexible member (2B) form a single part.

In yet another aspect of the invention, the pharmaceutical forms are selected from the group comprising ovula, tablets, capsules, pills, gels, suspensions, suppositories and the like.

The present invention also relates to an applicator (1) for delivery of pharmaceutical forms (4) into body holes, comprising a body (3), characterized in that it further comprises a dispensing mechanism (2) of the invention.

In one aspect, the dispensing mechanism (2) of the applicator (1) is arranged within the body (3), wherein the flexible member part (2C) of the dispensing mechanism (2) is immobilized in and/or in relation to the body (3), and the flexible member (2B) or a part thereof is accessible to a user for actuation.

In another aspect, the flexible member (2B) of the mechanism (2) is a rim, and the body (3) comprises diametrically opposed slots through which two separate and substantially opposite parts of said rim pass.

In another aspect of the invention, the body (3) comprises at least one elastic membrane surrounding the dispensing mechanism (2).

In yet another aspect, the body (3) has a tubular shape or a wavy shape.

In another aspect of the invention, the applicator (1) is disposable.

In a further aspect, the applicator (1) of the invention is reusable.

A disposable kit for delivery of pharmaceutical forms into body holes, comprising an applicator (1) of the present invention and a pharmaceutical form is disclosed.

A reusable kit for delivery of pharmaceutical forms into body holes, comprising an applicator (1) of the present invention, a pharmaceutical form and refills is also disclosed.

A kit as any of the preceding kits, further comprising a pair of disposable gloves is further disclosed.

The pharmaceutical forms used in any of the preceding kits are selected from the group comprising ovula, tablets, pills, capsules, gels, suspensions, suppositories and the like.

BRIEF DESCRIPTION OF THE DRAWINGS

Herein after, a detailed description of the invention is made with reference to the accompanying drawings, in which.

DETAILED DESCRIPTION OF THE INVENTION

For easiness of understanding of the invention, the present description is made with reference to accompanying FIGS. 1 to 4.

In the context of the present description, the term "comprising" (or "comprise") should be understood to mean "including, among others". As such, said term should not be construed as "consisting only of".

Still in the context of the present description, the use of expression "and/or" is intended to mean that both conditions occur or only one occurs. For example, the expression "before and/or during application" means "before and during application" or "before application" or "during application".

The present invention relates to a dispensing mechanism (2) and a delivery applicator (1) of pharmaceutical forms into body holes. In particular, it relates to a dispensing mechanism (2) and applicator (1) for intra-vaginal delivery.

Known applicators are not appropriate to introduce pharmaceutical forms such as, for example, ovula, tablets, capsules, pills, gels and suppositories, as they all work based on a cannula with a syringe-type plunger which requires manipulation and application with both hands, which, in adverse situations, can accidentally actuate the plunger before the cannula is properly positioned into the body hole and, in particular, into the vagina, resulting in an ineffective treatment.

The present invention aims to improve and simplify dispensing of pharmaceutical forms into body holes, making it possible to realize the operation with one hand only, by means of a novel dispensing mechanism (2) arranged within an ergonomic applicator body (3).

This applicator (1) is intended for dispensing pharmaceutical forms selected from the group comprising ovula, tablets, capsules, pills, gels, suspensions, suppositories and the like.

The applicator (1) of the present invention provides the following advantages compared to prior art devices:

ease and comfort of use, due to the design of the new dispensing mechanism of the invention, safety and ergonomics, efficiency by ensuring the delivery precisely in the desired location, versatility, allowing the accommodation of all pharmaceutical forms and being able to be used in different delivery routes with a number of pharmaceutical forms, value for money due to the simplicity of construction of the new dispensing mechanism and assembly of the applicator, allowing economic production on an industrial scale.

Figure 1:
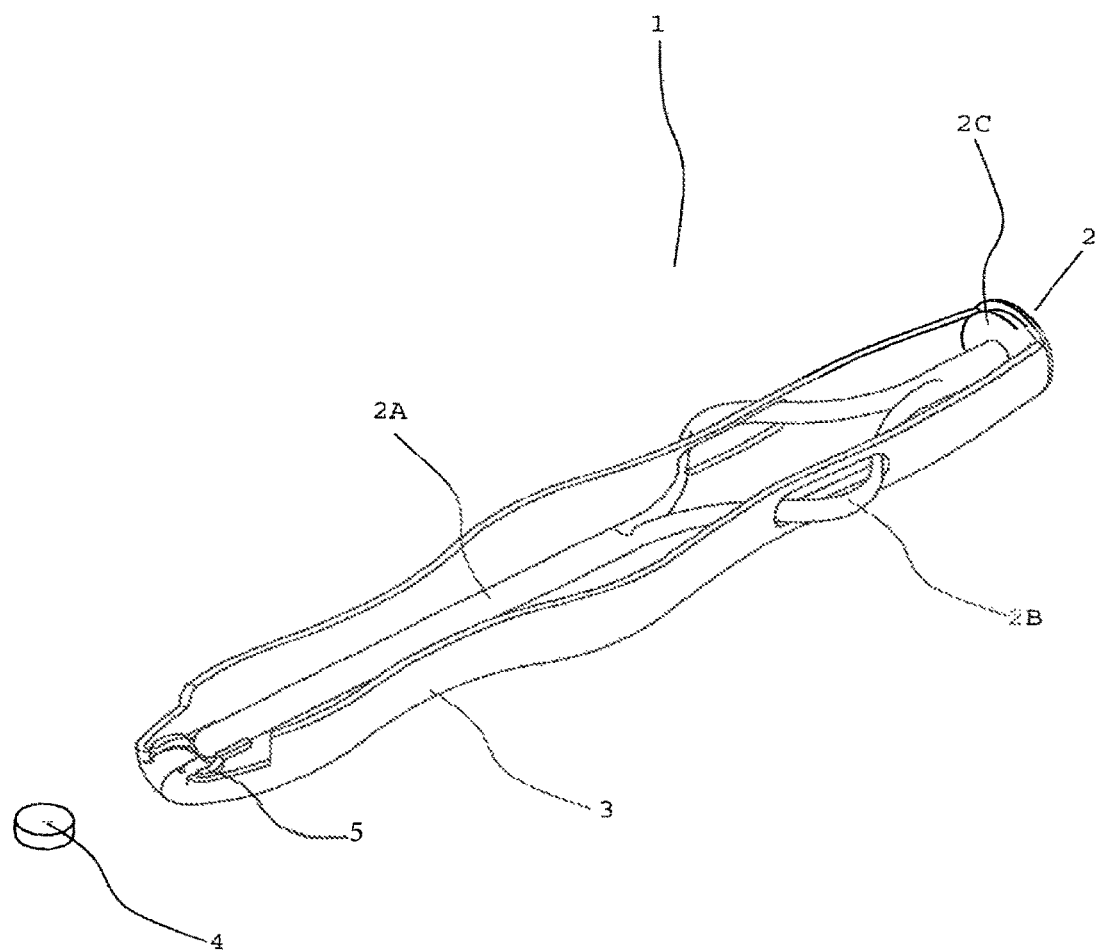
FIG. 1 is a perspective sectional view of a preferred embodiment of the applicator of the present invention with a part of the body cut out in order to show the arrangement of the dispensing mechanism within the body of the applicator.

The applicator (1) of the invention comprises a body (3) into which a pharmaceutical form dispensing mechanism (2) is arranged, such as illustrated in FIG. 1.

Said applicator body (3) has any type of suitable gripping means such as, for example, flexible forceps (5), to hold any of the solid pharmaceutical forms (4) and thereby avoiding a possible accidental release of same (4) before and/or during application.

Components (2, 3) of the applicator (1) of the present invention can be manufactured, for example, in plastic, metallic, ceramic, composite material or combinations thereof. Plastic is the preferred material to be used.

Several arrangements of the applicator are provided taking into account the ergonomics associated with the intended use.

Figure 4:
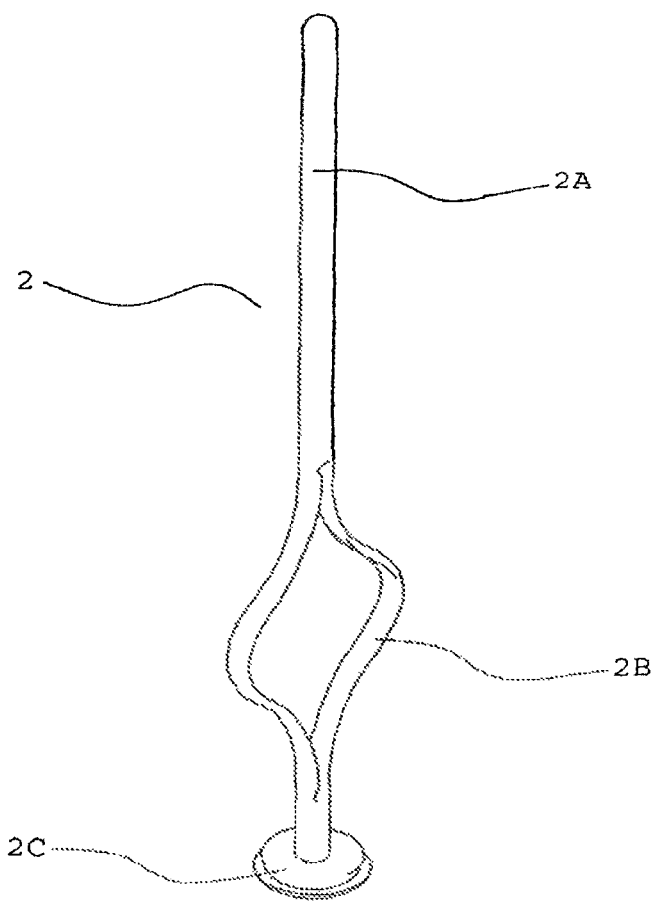
FIG. 4 is a schematic illustration of the preferred dispensing mechanism of the present invention.

With reference to FIG. 4, the pharmaceutical form dispensing mechanism (2) is one of the components of the applicator (1) of the present invention, and its design is important from the operative point of view, as it enables using the applicator (1) with only one hand in a comfortable and safe way.

In fact, as mentioned above, conventional syringe type mechanisms are not practical for those with limited motion and/or strength, such as, for example, older or paraplegic patients. Thus, the dispensing mechanism (2) of the present invention is designed as a component of the applicator (1) that overcomes these limitations.

Still with reference to FIG. 4, the pharmaceutical form dispensing mechanism (2) of the invention comprises a rod (2A) connected to a flexible member (2B). The rod (2A) has a first and a second end, the first end being cooperatively connected to said flexible member (2B), and the second end being free from constraints in order to move axially.

Said flexible member (2B) has a rounded or angular shape, and is a deformable member having shape memory. Flexible member (2B) extends in a direction perpendicular to the direction of a compression force applied to it and recovers its original shape when said compression force is withdrawn.

In the context of the present invention, the expression "deformable member provided with shape memory" relates to a part having a shape as defined herein below, which part is able to be deformed by applying a manual force, namely a force applied by the fingers of a hand of a patient or person with some limitations or physical disabilities, which deformation ceases at the moment in which said force is stopped, and the part recovers its original shape once the user removes the force that has been applied to it.

Preferably, the flexible member (2B) has a shape selected from the group comprising ring, semi-circular, oval, semi-oval, spherical calotte, V shape, and the like.

Preferably, the rod (2A) and the flexible member (2B) are integral into a single part, which allows simplifying the production process of the dispensing mechanism (2) and thus reducing its production cost.

In operative terms, having a part (2C) of the flexible member constrained to prevent any movement thereof, and such part (2C) being substantially opposite to said first end of the rod (2A) which is connected to the flexible member (2B), when the flexible member (2B) is pressed it extends due to the effect of compression force on and imparts the movement associated with said extension to the rod (2A), to which it is connected, thereby providing a forward axial movement to said rod (2A) which therefore behaves as a syringe plunger. When the compression force is withdrawn from the flexible member (2B), this latter recovers its original shape, thereby causing the rod (2A) to move back.

The design of the present dispensing mechanism (2) allows avoiding the known positional difficulties experienced by users when operating prior art applicators, as it is namely the situation of users of intra-vaginal applicators. In fact, the applicator (1) of the present invention, due to the actuation is done in a direction substantially perpendicular to the displacement direction of the rod (2A), allows a totally distinct handling from that practiced in prior art applicators in which the actuation direction occurs in the same direction of the displacement of the respective plungers. Moreover, this solution in addition to facilitate the introduction of the applicator (1) and its operation, further allows reducing the dimensions of the applicator (1) to those that are really indispensable from a functional point of view.

Figure 3:
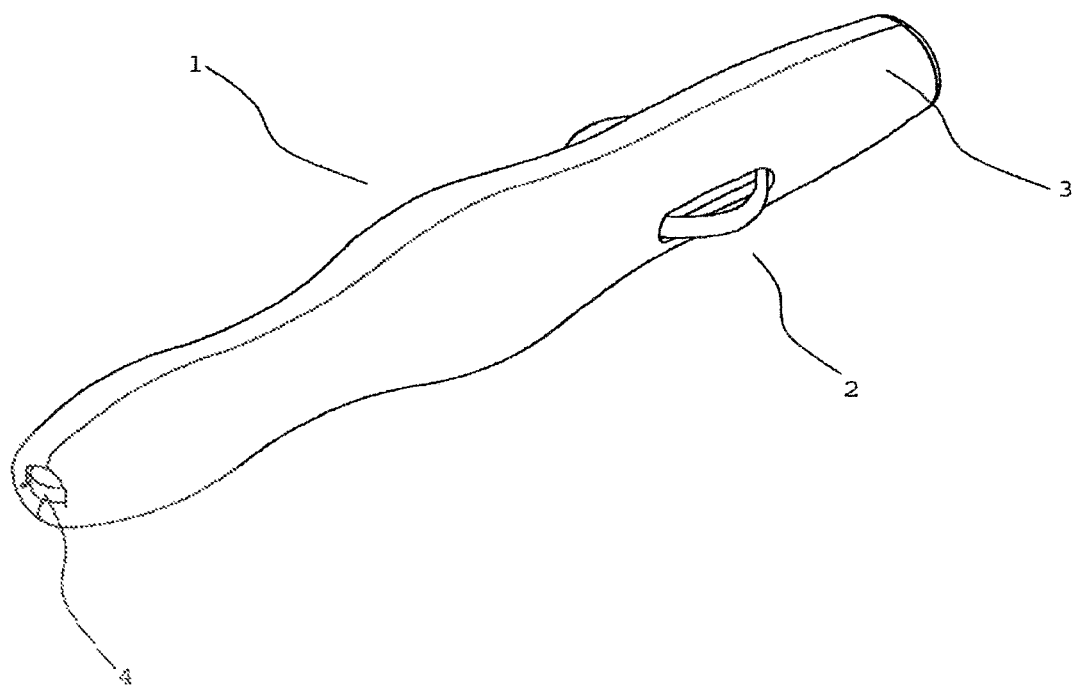
FIG. 3 is a perspective view of the applicator of FIGS. 1 and 2 loaded with a pharmaceutical form.

As can be seen in FIGS. 1 and 3, the dispensing mechanism (2) should be arranged within the body (3) of the applicator (1) such that the flexible member (2b) or a part thereof remains accessible to the user for the purpose of actuating the same, and the flexible member part (2C) of the mechanism (2) is immobilized in and/or in relation to the body (3) of the applicator.

As will be appreciated, a number of modes for arranging the dispensing mechanism (2) into body (3) of the applicator (1) are possible, depending on the desired configuration for the flexible member (2B) and/or the body (3) itself.

The body (3) of applicator may be of any ergonomically shape suitable to the intended application, in particular it can be, for example, tubular or it can have a wavy shape.

The body (3) of applicator may be designed so as to provide access to the dispensing mechanism (2), for actuation, in particular, by means of slots through which parts of the dispensing mechanism (2) pass or by means of elastic membranes surrounding the dispensing mechanism (2) and simultaneously allowing the actuation of the latter by a user.

A design of any other configuration of the applicator body (3) which allows manual access to the dispensing mechanism (2), allowing or not visual access to the latter, is envisaged.

Still in relation to the applicator body (3), it should comprise an outlet nozzle from which the pharmaceutical form exits and whose configuration conforms to the type and/or shape of the pharmaceutical form to be delivered. As previously mentioned, in case of solid pharmaceutical forms (4), said outlet nozzle of the applicator body (3) has, for example, flexible forceps adapted to hold any of the solid pharmaceutical forms (4), and thereby avoid a possible accidental release of the same (4) before and/or during application.

The applicator (1) of the present invention may be disposable or reusable, according to market needs and type of application intended.

The present invention also relates to a kit comprising the applicator of the invention, having a single pharmaceutical form for a single application.

The present invention also relates to an applicator kit having refills of the pharmaceutical form for multiple applications.

The present invention further relates to any of the previous kits further comprising at least one pair of disposable gloves.

Figure 2:
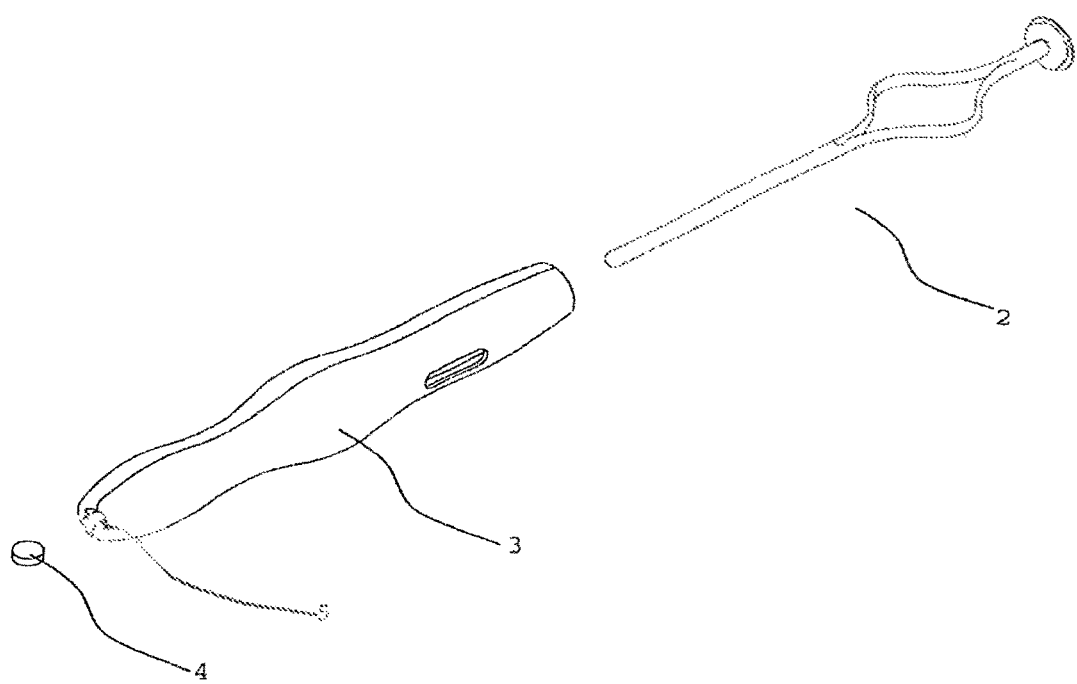
FIG. 2 is an exploded view of the applicator of FIG. 1, showing a pharmaceutical form, the body of the applicator, and the dispensing mechanism.

In a preferred embodiment, illustrated in FIGS. 1 to 3, which takes into account production requirements of the present applicator (1), this is intended to intra-vaginal application and essentially consists of three parts, two of which form, by coupling or fitting, the applicator body (3) having a wavy shape, and the third part consists of said pharmaceutical form dispensing mechanism (2). In terms of assembly, the dispensing mechanism (2) is arranged in a first part of the body (3), then the second part of body (3) being assembled by fitting or coupling in said first part so as to provide the finalized shape to the body (3) of applicator (1).

In this embodiment, the dispensing mechanism (2) is of ring shape and the body (3) of applicator comprises 2 diametrically opposite slots, through which two substantially opposite separate parts of the ring of the mechanism (2) pass, thus allowing to arrange the dispensing mechanism (2) within the body (3) while providing access to mechanism (2) from the outside of said body (3), so as to allow the actuation thereof to the user.

Regarding the operation mode of the applicator (1) of the preferred embodiment, the user can apply it, for example in a sitting position, using the fingers of one hand to open vaginal labia. Then, with the other hand, she inserts the applicator into the vagina. Then, she releases the vaginal labia, which constrict themselves, allowing suitable positioning and fixation of the applicator for subsequent dispensing of the pharmaceutical form, for instance, a ovulum.

At the opposite end to the dispensing end of the applicator body (3), the user presses the dispensing mechanism (2), which protrudes from the body (3), with the same hand which had inserted the applicator into the vagina, so as to actuate said mechanism (2) and thereby complete the intra-vaginal insertion process of said ovulum.

The invention claimed is:

1. An applicator for delivery of a solid pharmaceutical form into a body hole comprising
    an applicator body comprising a dispensing end; and
    a dispensing mechanism arranged within the applicator body,
    wherein the dispensing mechanism comprising
        a rod having a first end and a second end, the second end of the rod is positioned at the dispensing end;
        flexible forceps positioned for holding the solid pharmaceutical form, the flexible forceps being positioned at the dispensing end of the applicator body;
        a flexible member connected to the first end of the rod, the flexible member is able to be deformed and is provided with shape memory, and has a rounded or angular shape, and the flexible member or a part of the flexible member is accessible through the applicator body to a user for actuation of the dispensing mechanism without movement of the applicator body to dispense the solid pharmaceutical form; and
        a flexible member part of the flexible member being opposite to said first end of the rod, the flexible member part is immobilized in relation to the applicator body at an end opposite the dispensing end,
    wherein the flexible member extends in a direction perpendicular to the direction of a compression force applied to the flexible member by the user for actuation, and recovers the original shape of the flexible member when said compression force is withdrawn,
    wherein the compression force applied to the flexible member for actuation being perpendicular to a displacement direction of the rod, thereby providing forward axial movement to the rod toward the dispensing end when the compression force is applied to the flexible member and providing rearward axial movement to the rod away from the dispensing end when the compression force to the flexible member is withdrawn,
    wherein the solid pharmaceutical form is configured to be positioned at the second end of the rod to be gripped by the flexible forceps, such that operation of the dispensing mechanism by the user applying the compression force to the flexible member causes dispensing of the solid pharmaceutical form by the rod pushing the solid pharmaceutical form out of the applicator body without movement of any portion of the applicator body.

2. The applicator according to claim 1, wherein the flexible member has a shape selected from the group consisting of a ring, semicircular, oval, semi-oval, spherical calotte and V shape.

3. The applicator according to claim 1, wherein the rod and the flexible member form a single part.

4. The applicator according to claim 1, wherein the solid pharmaceutical form is selected from the group consisting of ovula, tablets, capsules, pills, and suppositories.

5. The applicator according to claim 1, wherein the flexible member of the mechanism is a rim, and the applicator body comprises diametrically opposed slots through which two separate and substantially opposite parts of said rim pass.

6. The applicator according to claim 1, wherein the applicator body has a tubular shape or a wavy shape.

7. The applicator according to claim 1, wherein the applicator is disposable.

8. The applicator according to claim 1, wherein the applicator is reusable.

9. A disposable kit for delivery of a solid pharmaceutical form into a body hole, wherein the disposable kit comprises the applicator of claim 1 and the solid pharmaceutical form.

10. The kit according to claim 9, wherein the disposable kit further comprises at least a pair of disposable gloves.

11. The kit according to claim 9, wherein the solid pharmaceutical form and refills of said solid pharmaceutical form are selected from the group consisting of ovula, tablets, pills, capsules, and suppositories.

12. A reusable kit for delivery of solid pharmaceutical forms into body holes, wherein the reusable kit comprises an applicator of claim 1, the pharmaceutical form and refills of said pharmaceutical form.

* * * * *